(12) United States Patent
Vial

(10) Patent No.: US 10,047,319 B2
(45) Date of Patent: Aug. 14, 2018

(54) 1-ISOPROPOXY-1-OXOPROPAN-2-YL PIVALATE AS PERFUMING INGREDIENT

(71) Applicant: FIRMENICH SA, Geneva (CH)

(72) Inventor: Christian Vial, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/904,328

(22) PCT Filed: Jul. 3, 2014

(86) PCT No.: PCT/EP2014/064138
§ 371 (c)(1),
(2) Date: Jan. 11, 2016

(87) PCT Pub. No.: WO2015/003985
PCT Pub. Date: Jan. 15, 2015

(65) Prior Publication Data
US 2016/0130526 A1 May 12, 2016

(30) Foreign Application Priority Data

Jul. 8, 2013 (EP) .................................... 13175628

(51) Int. Cl.
| | |
|---|---|
| *C11B 9/00* | (2006.01) |
| *A61Q 13/00* | (2006.01) |
| *A61L 9/01* | (2006.01) |
| *C07C 69/67* | (2006.01) |
| *C11D 3/50* | (2006.01) |
| *A61K 8/37* | (2006.01) |
| *A61Q 19/00* | (2006.01) |
| *C07C 69/34* | (2006.01) |
| *C11D 3/20* | (2006.01) |
| *A61Q 5/02* | (2006.01) |
| *A61Q 5/06* | (2006.01) |
| *A61Q 9/02* | (2006.01) |
| *A61Q 19/10* | (2006.01) |

(52) U.S. Cl.
CPC .............. *C11B 9/0019* (2013.01); *A61K 8/37* (2013.01); *A61L 9/01* (2013.01); *A61Q 13/00* (2013.01); *A61Q 19/00* (2013.01); *C07C 69/34* (2013.01); *C07C 69/67* (2013.01); *C11D 3/2093* (2013.01); *C11D 3/50* (2013.01); *A61K 2800/10* (2013.01); *A61Q 5/02* (2013.01); *A61Q 5/06* (2013.01); *A61Q 9/02* (2013.01); *A61Q 19/10* (2013.01)

(58) Field of Classification Search
CPC ...... A61K 8/37; A61K 2800/10; A61Q 19/00; A61Q 13/00; A61Q 9/02; A61Q 5/06; A61Q 5/02; A61Q 19/10; A61L 9/01; C07C 69/67; C07C 69/34; C11D 3/2093; C11D 3/50; C11B 9/0019
See application file for complete search history.

(56) References Cited

U.S. PATENT DOCUMENTS

| | | | |
|---|---|---|---|
| 6,509,312 B1 | 1/2003 | Giersch | |
| 2009/0326095 A1* | 12/2009 | Badejo | ................... A61L 15/58 523/118 |
| 2011/0097291 A1* | 4/2011 | Vial | ....................... C07C 69/67 424/65 |

FOREIGN PATENT DOCUMENTS

| | | |
|---|---|---|
| EP | 1069176 B1 | 9/2004 |
| WO | WO2009147565 A1 | 12/2009 |

OTHER PUBLICATIONS

International Search Report and Written Opinion, application PCT/EP2014/064138, mailed Oct. 6, 2014.
Wagner et al., Synthesis, 1998, n° 6, 883-888.

* cited by examiner

*Primary Examiner* — Robert S Cabral
(74) *Attorney, Agent, or Firm* — Winston & Strawn LLP

(57) ABSTRACT

The present invention concerns the use of 1-isopropoxy-1-oxopropan-2-yl pivalate, in the form of any one of its stereoisomers or a mixture thereof, as perfuming ingredient to impart odor notes of the floral and fruity type.

6 Claims, No Drawings

1-ISOPROPOXY-1-OXOPROPAN-2-YL PIVALATE AS PERFUMING INGREDIENT

TECHNICAL FIELD

The present invention relates to the field of perfumery. More particularly, it concerns the use of 1-isopropoxy-1-oxopropan-2-yl pivalate, in the form of any one of its stereoisomers or a mixture thereof, as perfuming ingredient. The present invention comprises the invention's compound as part of a perfuming composition or of a perfuming consumer product.

PRIOR ART

To the best of our knowledge, the invention's compound as such is novel.

WO2009/147565, although not disclosing specifically the invention's compound, reports perfuming compounds of a general formula encompassing the invention's compound; however said prior art compounds are described as being of the fruity type, while the present compound does have an additional and surprising floral note.

DESCRIPTION OF THE INVENTION

We have now surprisingly discovered that 1-isopropoxy-1-oxopropan-2-yl pivalate, of formula

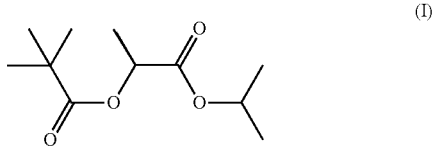 [SMILES: CC(C)OC(=O)C(C)(C)OC(=O)C(C)(C)C]

(I)

in the form of any one of its stereoisomers or a mixture thereof;
can be used as perfuming ingredient, for instance to impart odor notes of the floral and fruity type.

For the sake of clarity, by the expression "any one of its stereoisomers", or the similar, it is meant the normal meaning understood by a person skilled in the art, i.e. that the invention's compound can be a pure enantiomer (e.g. the one of configuration S or R).

As specific examples of the invention's compounds, one may cite, as non-limiting example, (−)-(S)-1-isopropoxy-1-oxopropan-2-yl pivalate which possesses an odor having a floral, rosy/geranium type note having also a linalool, citronellol, geranyl acetate aspect, as well as a fruity, citrusy type note having lemon, bergamot aspects. The overall hedonic effect is an interesting rosy/geranium and fruity impression.

As other example, one may cite (+)-(R)-1-isopropoxy-1-oxopropan-2-yl pivalate, which possesses an odor similar to the one of the S enantiomer but distinguishing itself by a slightly more pronounced fruity note and being less raising than the S enantiomer.

As other example, one may cite 1-isopropoxy-1-oxopropan-2-yl pivalate, which possesses an odor similar to the one of the S enantiomer but distinguishes itself surprisingly by a slightly more pronounced floral/rosy note.

According to a particular embodiment of the invention, the compounds of formula (I) are (−)-(S)-1-isopropoxy-1-oxopropan-2-yl pivalate or 1-isopropoxy-1-oxopropan-2-yl pivalate.

When the odor of the invention's compounds is compared with that of the prior art compounds described in WO2009/147565, such as propyl (S)-2-(isobutyryloxy)propanoate, (−)-(S)-1-isopropoxy-1-oxopropan-2-yl isobutyrate or (−)-(S)-1-ethoxy-1-oxopropan-2-yl pivalate, then the invention's compounds distinguish themselves by having a floral (rosy/geranium) note which is absent, or not significant, in the prior art compounds. Said floral note is a distinguishing character of the odor profile of the invention's compound and not a simple aspect or shade, as shown in the examples.

The present invention's compounds do distinguish also by having a different type of fruity notes (in the present case of the citrusy type) when compared to the prior art compounds. Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as a perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned perfuming consumer products may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the product to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 1% to 50% by weight, or even more, of the compounds of the invention based on the weight of the composition into which they are incorporated. Concentrations lower than these, such as in the order of 0.05% to 20% by weight, can be used when these compounds are incorporated into perfuming consumer product, percentage being relative to the weight of the article.

The invention's compounds can be prepared according to a method as described in the examples herein below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

Preparation of (−)-(S)-1-isopropoxy-1-oxopropan-2-yl pivalate

To a solution of S-(−)-isopropyl lactate (68.1 g, 0.5 mole, $[α]^{20}_D$=−3.2°, 2.5%, $CHCl_3$), triethylamine (61.3 g, 0.6 mole) in dichloromethane (800 ml) at 0° was slowly added pivaloyl chloride (67.0 g, 0.55 mole). After 24 hours at room temperature, the mixture was quenched with 10% HCl (200 ml) and crushed ice (100 g) and then the organic phase was washed with aqueous $NaHCO_3$, water and dried over $Na_2SO_4$. Evaporation of dichloromethane provided a residue (96.7 g) which was rapidly distilled using a Vigreux column (B.p.$_{12\ mbars}$=80-85°) and then fractionated using a Fischer column (B.p.$_{12\ mbars}$=83-85°) to give 51.1 g (yield=47%) of pure (−)-(S)-1-isopropoxy-1-oxopropan-2-yl pivalate.

$[α]^{20}_D$=−32.6° (3.1%, CHCl3).

$^1$H-NMR: 1.23 (d: J=6, 3H); 1.24 (s, 9H); 1.26 (d: J=6, 3H); 1.47 (d: J=7, 3H); 4.99 (q: J=7, 1H); 5.05 (sept., J=6, 1H).

$^{13}$C-NMR: 16.7 (q), 21.6 (q), 21.7 (q), 27.0 (3q), 38.5 (s), 68.6 (d), 68.8 (d), 170.5 (s), 177.8 (s).

The R enantiomer or the racemate can be obtained exactly by the same method except that the starting material used is R-(+)-isopropyl lactate or isopropyl lactate respectively.

Example 2

Preparation of a Perfuming Composition

A perfuming composition for a "all purpose cleaner" was prepared by admixing the following ingredients:

| Parts by weight | Ingredient |
|---|---|
| 900 | Isobornyl acetate |
| 300 | Benzyl acetate |
| 200 | Anisic aldehyde |
| 50 | Aldehyde mna |
| 50 | Methyl anthranilate |
| 50 | 10%* 4-(4-Hydroxy-1-phenyl)-2-butanone |
| 20 | Borneol |
| 30 | Citronellyl nitrile |
| 300 | Coranol ™ [1] |
| 100 | Coumarine |
| 200 | (1'R,E)-2-Ethyl-4-(2',2',3'-trimethyl-3'-cyclopenten-1'-yl)-2-buten-1-ol |
| 100 | Eugenol |

-continued

| Parts by weight | Ingredient |
|---|---|
| 100 | 1,3-Benzodioxole-5-carbaldehyde |
| 350 | Lavandin grosso |
| 50 | Menthone |
| 20 | Crystal moss |
| 50 | Rose oxide |
| 150 | Patchouli oil |
| 150 | Phenethylol |
| 400 | Orange essential oil |
| 500 | Amyl salicylate |
| 700 | Benzyl salicylate |
| 450 | Terpineol |
| 250 | Terpinolene |
| 30 | Yara yara |
| 400 | Lemon essential oil |
| 100 | Ylang oil |
| 6000 | |

*in dipropyleneglycol
[1] 4-cyclohexyl-2-methyl-2-butanol; origin: Firmenich SA, Geneva, Switzerland The effect obtained by the addition to the above composition of 4000 parts by weight of the following compounds was described as:

a) (−)-(S)-1-isopropoxy-1-oxopropan-2-yl pivalate introduced a fruitiness and a floral-geranium aspect to the fragrance. The geranium aspect, obtained when adding the invention's compound was comparable to the addition of a 80/20 mixture of propyl (S)-2-(1,1-dimethylpropoxy) propanoate (see EP 1069176) and citronellol (3200 parts 800 parts resp.);

b) propyl (S)-2-(isobutyryloxy)propanoate (WO2009/147565) imparted no floral notes but a similar fruitiness as propyl (S)-2-(1,1-dimethylpropoxy)propanoate (see EP 1069176) but less freshness overall;

c) (−)-(S)-1-ethoxy-1-oxopropan-2-yl pivalate (WO2009/147565) imparted no floral notes but a butyric fruitiness, reminiscent of apple and strawberry;

d) ethyl (S)-2-(propanoyloxy)propanoate (WO2009/147565) imparted no floral notes but a fruity/green, metallic, vinous/rhubarb note; or e) (−)-(S)-1-isopropoxy-1-oxopropan-2-yl isobutyrate (WO2009/147565) imparted no floral notes but only a butyric fruitiness reminiscent of apricot.

Example 3

Preparation of a Perfuming Composition

A perfuming composition for a "eau de cologne" type, was prepared by admixing the following ingredients:

| Parts by weight | Ingredient |
|---|---|
| 250 | Wormwood oil |
| 1500 | Bergamot oil |
| 2200 | Lemon oil |
| 300 | Lavender oil |
| 150 | Mandarin oil |
| 100 | Crystal moss |
| 100 | Muscenone ™ Delta[1] |
| 700 | Petitgrain |

-continued

| Parts by weight | Ingredient |
|---|---|
| 2000 | Orange oil |
| 300 | Rosemary oil |
| 100 | Clary sage oil |
| 300 | Neroli oil |
| 8000 | |

[1])3-methyl-5-cyclopentadecen-1-one; origin: Firmenich SA, Geneva, Switzerland

The effect obtained by the addition to the above composition of 2000 parts by weight of to the following compounds was described as:
a) (−)-(S)-1-isopropoxy-1-oxopropan-2-yl pivalate imparted a rounder citrus notes and fruitier and added a floral geranium/rose note. The same floral effect introduced by the invention's compound was obtained by adding a mixture of roughly 75% propyl (S)-2-(1,1-dimethylpropoxy)propanoate (see EP 1069176) and 25% Citronellol (1500 parts and 500 parts respectively), but not by adding 2000 parts of propyl (S)-2-(1,1-dimethylpropoxy)propanoate (see EP 1069176) alone;
b) propyl (S)-2-(isobutyryloxy)propanoate (WO2009/147565) imparted no floral notes but pushed the aromatic notes, and added less fruitiness to the citrus notes than the invention compound;
c) Ethyl (S)-2-(propanoyloxy)propanoate (WO2009/147565) imparted no floral notes but makes the composition bitter green and harsh; or
d) (−)-(S)-1-ethoxy-1-oxopropan-2-yl pivalate (WO2009/147565) imparted no floral notes but added a sweet, butyrique fruitiness which, combined with the crystal moss, creates a typical fruity Chypre effect.

What is claimed is:
1. A method to impart floral odor notes to a perfuming composition or a perfumed article, which method comprises adding to said composition or article an effective amount of at least a compound of formula (I),

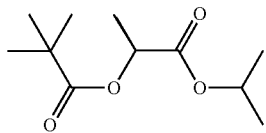

in the form of any one of its stereoisomers or a mixture thereof to confer or impart floral odor properties to the composition or article.

2. The method as recited in claim 1, wherein said compound is (−)-(S)-1-isopropoxy-1-oxopropan-2-yl pivalate or 1-isopropoxy-1-oxopropan-2-yl pivalate.

3. The method of claim 1, wherein the at least one compound of Formula I is added to a perfuming composition comprising at least one ingredient selected from the group consisting of a perfumery carrier and a perfumery base; and optionally, at least one perfumery adjuvant.

4. The method of claim 1, wherein the at least one compound of Formula I is added to a perfuming consumer product that is a perfume, a fabric care product, a body-care product, an air care product or a home care product.

5. The method of claim 1, wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

6. The method of claim 1, wherein the at least one compound of Formula I is added to said composition or article in an amount effective to provide a rosy or rosy/germanium floral note.

* * * * *